US008481010B2

United States Patent
Schoon et al.

(10) Patent No.: US 8,481,010 B2
(45) Date of Patent: Jul. 9, 2013

(54) COVALENTLY BONDING NAIL PRIMER

(75) Inventors: Douglas D. Schoon, Dana Point, CA (US); James Duff, Escondido, CA (US); Thong Vu, Vista, CA (US); Andry Hong, Monterey Park, CA (US); Daniel Moore, Escondido, CA (US)

(73) Assignee: Creative Nail Design, Inc., Vista, CA (US)

( * ) Notice: Subject to any disclaimer, the term of this patent is extended or adjusted under 35 U.S.C. 154(b) by 104 days.

(21) Appl. No.: 12/127,769

(22) Filed: May 27, 2008

(65) Prior Publication Data

US 2008/0226573 A1    Sep. 18, 2008

Related U.S. Application Data

(63) Continuation of application No. 10/383,826, filed on Mar. 7, 2003, now abandoned.

(51) Int. Cl.
*A61K 8/18* (2006.01)
(52) U.S. Cl.
USPC ............................................................ 424/61
(58) Field of Classification Search
None
See application file for complete search history.

(56) References Cited

U.S. PATENT DOCUMENTS

| 3,417,054 A | 12/1968 | Grosser et al. |
| 4,766,005 A | 8/1988 | Montgomery et al. |
| 5,098,696 A | 3/1992 | Montgomery |
| 5,523,076 A | 6/1996 | Schoon |
| 5,603,924 A | 2/1997 | Montgomery |
| 5,738,843 A | 4/1998 | Montgomery |
| 5,772,988 A | 6/1998 | Pagano et al. |
| 5,798,426 A | 8/1998 | Anton et al. |
| 5,830,442 A | 11/1998 | Beaver |
| 5,939,514 A | 8/1999 | Brown et al. |
| 6,355,720 B1 | 3/2002 | Canard et al. |

*Primary Examiner* — Anand Desai
*Assistant Examiner* — Melissa Mercier
(74) *Attorney, Agent, or Firm* — Venable LLP; Keith G. Haddaway

(57) ABSTRACT

The present invention relates generally to the field of primers and adhesion promoters. More specifically, the primer of the present invention is comprised of one or more multi-carbonylated methacrylates. In a preferred embodiment, a non-ketone polar solvent is also employed. The resulting composition eliminates primer related discoloration of artificial nail enhancements, eliminates the potential for corrosion of skin and nails, and eliminates risk of chemical burn injury, while providing stronger adhesion than currently available primers.

12 Claims, No Drawings

COVALENTLY BONDING NAIL PRIMER

This is a continuation of U.S. patent application Ser. No. 10/383,826, filed Mar. 7, 2008, which itself claims priority to Intl. Patent Appl. No. PCT/US2004/006874, filed Mar. 4, 2004, both of which are incorporated herein in their entirety.

FIELD OF THE INVENTION

The present invention relates generally to the field of primers and adhesion promoters. More specifically, the primer of the present invention is comprised of one or more multi-carbonylated methacrylates. In a preferred embodiment, a non-ketone polar solvent is also employed.

The disclosed primer has particular utility as a primer for nails and other proteinaceous substrates. For a number of years, nail technicians have searched for acceptable substitutes for extremely corrosive primers that cause yellowing of nail enhancements. These (meth)acrylic acid-based primers (and all other current nail primers) rely on relatively weak hydrogen bonding to achieve interfacial bonding. In contrast, the present invention is a significant advance in the art—a non-corrosive, non-yellowing primer that covalently bonds to the nail plate. In other words, the disclosed primer will not corrode or irritate the surrounding tissue or nail plate, nor will it discolor the artificial nail enhancement, while simultaneously bonding the enhancement to the keratin substrate far more strongly than currently available products.

BACKGROUND OF THE INVENTION

The nail plate (i.e., the natural nail) is primarily composed of keratin, a water-insoluble, fibrous protein that is a major structural component of skin, hair, wool, silk, feathers, scales, nails and hooves. While keratins can obviously differ greatly in their amino acid makeup, hard keratins may all be generally characterized as cross-linked polypeptides. Alpha-keratins such as nails and hooves may be further characterized by their relatively higher percentages of the amino acid cysteine. Typically, the alpha-helix coils of the polypeptides are cross-linked with disulphide bonds between adjacent cysteines. The resulting plate-like cells are cemented to each other with a sticky substance and held together by rivet-like structures called desmosomes. Many cell layers adhere to each other to form the nail plate—a structure that resembles a brick and mortar wall.

Primers are adhesion promoters that improve adhesion by increasing interfacial compatibility between surfaces, e.g., the nail plate and an applied coating. For example, a coating of nail polish will resist chipping and peeling if a good base coat is used. Base coats are more compatible with the nail plate than the nail polish. Base coats act as the "go-between" or "anchor", to improve adhesion.

Primers are also frequently used with artificial nail enhancements since acrylic nail products normally have poor adhesion to nail plates. In general, nail plate primers can be thought of as double-sided sticky tape, joining the nail plate to the nail enhancement. The nail plate surface is made up of chemical groups possessing specific structures. Primer molecules must match the chemical and structural characteristics of the nail plate. More particularly, one end of the primer is reactive with the methacrylate monomers. With these types of primers, physical abrasion of the nail plate is required to achieve proper levels of adhesion to the keratin substrate. Moreover, these acids are corrosive, and if used improperly they can cause damage to the nail plate and surrounding tissue. These acids can also cause discoloration of the nail enhancement and are a leading cause of nail product discoloration. This invention eliminates a large percentage of discoloration problems for professional nail technicians. But even more importantly, in response to a number of chemical burn injuries, primarily to children, the Consumer Product Safety Commission recently issued a regulation requiring child-resistant packaging for all household products containing more than 5% methacrylic acid. However, child-resistant caps increase the risk of spills in the salon as Nail Professionals struggle to remove the cap. This invention solves both the burn injury and child-resistant cap issues because it utilizes a non-corrosive solvent, while still providing the desired adhesion properties.

Commercially available nail primers rely solely on hydrogen bonding. Hydrogen bonding on organic substrates such as keratin typically depends on the interaction between an oxygen or nitrogen atom that is covalently bonded to the upper surface of the nail plate and a hydrogen atom, covalently bonded to methacrylic acid, which is covalently linked to the polymer. A special type of interaction called a hydrogen bond exists between the interfaces of these dissimilar surfaces. Hydrogen bonds are types of attractive, intermolecular bonds that are characteristic of atoms with high electonegativity, i.e. fluorine, oxygen, sulfur, and nitrogen. They are many times weaker than the weakest covalent bond, which is found between a carbon and acidic hydrogens such as C—H as found in chloroform and acetylene. This weakness accounts for the attraction between the acidic hydrogen and a nearby organic, acidic hydroxyl group of acrylic or methacrylic acid primer, as well as the inherent relative weakness of hydrogen bonds. The overall strength of the hydrogen bond is determined by the strength of this relatively weak carbon/hydrogen bond. It is a controlling factor in hydrogen bond strength. Therefore, when acidic primers are used, the weakest adhesive link will exist between an oxygen molecule on the keratin surface and the acidic hydrogen of (meth) acrylic acid. Since covalent bonds are many times stronger than hydrogen bonding, improvements in adhesive bond strength can be achieved by eliminating the hydrogen bond and replacing it with a stronger, more permanent, organic covalent bond.

It is clear from the foregoing that there are three fundamental problems with currently available methacrylic primers and acrylic acid adhesion promoters. First is the corrosive nature of their primary component, methacrylic acid. Second, they create temporary hydrogen bonds that are inherently weaker than covalent bonds, leading to a weaker interfacial adhesive bond between the natural nail plate and the primer molecule, with a stronger adhesive bond between the primer molecule and the polymer chain of the nail enhancement. Third, acid-based primers are a primary cause of nail enhancement discoloration. Fourth, acid-based primers can result in chemical burn injuries.

SUMMARY OF THE INVENTION

The present invention solves the discoloration and corrosiveness problems associated with currently available primers by providing the first truly non-corrosive, non-yellowing covalently bonding primer. To date, nail primers and adhesion promoters have been corrosive due to their use of methacrylic or acrylic acid as the primary component. The present invention does not rely on these problematic components. Previous nail primers relied on relatively weak hydrogen bonding between nail and primer. The present invention employs components that are capable of creating continuous covalent bonds from the nail plate to the artificial nail enhancement, providing much improved adhesion. Additionally, previous nail primers were a prevalent cause of yellowing during "fills" when the primer came into direct contact with existing nail enhancement product on the natural nail. When using traditional primers, Nail Professionals must take great care to avoid the acid-based primer coming into contact with the artificial nail. Every two weeks when the artificial nail is "filled in" in the areas of new growth, dark yellow bands appear across the width of the nail enhancement when the (meth)acrylic acid primer comes into contact with the existing enhancement polymer.

These and other advantages are accomplished by the present invention, which relates to a primer comprised of one or more multi-carbonylated methacrylates. In a preferred embodiment, acetoacetoxy ethyl methacrylate ("AAEMA") is reacted with polyoxypropylenetriamine to produce an imine, or Schiff base, in an equilibrium reaction. In alternative embodiments, triethyleneglycoldiamine or other primary amines can be used instead of triethyleneglycoldiamine to achieve similar results. Simultaneous with this imine reaction, an amine group of the polyoxypropylenetriamine may also react with a carbonyl ester group of AAEMA to form an amide. Finally, the Schiff base undergoes a further electron rearrangement reaction in which an electron shifts to the beta carbon of the acetoacetoxy group (as shown below).

The resulting composition does not exhibit undesirable corrosive properties and is not based on (meth)acrylic acid and, in fact, contains no acidic functionality. Moreover, the disclosed primer provides stronger adhesion than any commercially available nail primer because it allows certain amino acid functional groups on the surface of the nail plate to covalently bond with carbonyl groups in the primer, creating much stronger linkages than can be achieved with hydrogen bonding of traditional primers.

Other objects, features, and characteristics of the present invention, as well as the methods of operation and functions of the related elements of the structure, and the combination of parts and economies of manufacture, will become more apparent upon consideration of the following detailed description, which forms part of this specification.

DETAILED DESCRIPTION OF THE INVENTION

As required, a detailed illustrative embodiment of the present invention is disclosed herein. However, techniques, systems, and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the present invention. The following presents a detailed description of a preferred embodiment (as well as some alternative embodiments) of the present invention.

The present invention is a dramatically improved primer that is particularly appropriate for use with nails. Herein, "nail" refers to not only human nails, but also nails and hooves of animals, and any other hard surface proteinaceous materials. The nail primer of the present invention is principally comprised of multi-carbonylated methacrylates dissolved in a suitable solvent or other delivery system. In a preferred embodiment of the present invention, the aforementioned components may be diluted in polar non-ketone solvents, however, non-polar solvents will work as well.

Various formulas have been tested by the applicant. One preferred embodiment comprises a polyether amine having a hydrophilic backbone, an acetoacetoxy methacrylate, and a polar non-ketone solvent. Of course, other components can be substituted as described below. One preferred polyether amine is triethyleneglycoldiamine. Again, other similar components (such as polyoxypropylenetriamine) can be utilized to achieve the results of this invention.

The preferred amines contain two or three primary amine functional groups, respectively. The primary amine functional groups are located on secondary carbon atoms at the ends of aliphatic polyether chains. Other primary amines, including monofunctional, difunctional and trifunctional amines, may be used in the present invention to achieve the desired results. Such primary amines include all polyetheramines, including but not limited to polyethyleneglycolamine, polyoxypropyleneamine, polyethyleneglycol-polyoxypropyleneamine, polyoxypropylenediamine, polyethyleneglycol-polyoxypropylenediamine, polyethyleneglycoltriamine, polyethyleneglycol-polyoxypropylenetriamine. Some examples of the above-mentioned components include, but are not limited to melamine, N,N-dimethylformamide, 1,5-diaminopentane and dibutylamine.

One particularly preferred multi-carbonylated methacrylate is acetoacetoxy ethyl methacrylate (referred to herein as "AAEMA").

The preferred solvent of the present invention is a non-ketone solvent. This ensures that the solvent will not react with the carbonyl group in the methacrylate, nor compete with the AAEMA carbonyl reaction. In nail applications, this helps prevent yellowing of the nail enhancement. However, in alternative embodiments of the invention where perhaps a slight coloration to the solvent blend would not be objectionable, a ketone solvent can be utilized if appropriate conditions are used during the bulk chemical reaction.

The solvent utilized in the present invention is also preferably a polar solvent to minimize the amount of discoloration which is observed when a non-polar solvent is utilized. However, in alternative embodiments of the present invention, a non-polar solvent can be utilized without compromising the integrity of the primer, which retains its adhesive and non-corrosive properties. Particularly preferred polar non-ketone solvents include ethanol and isopropanol. Other useful solvents include, but are not limited to, ethers, esters, glycol ethers, chlorinated solvents, siloxanes, tetrahydrofuran, methanol and other higher molecular weight alcohols, and suitable combinations thereof.

The weight percentages of the epoxy amine component in the tested formulas ranged from 0.75 to 2.5 percent, while the molar ratios of AAEMA to amine ranged from 1 to 5. Upon mixing, the carbonyl group of the acetoacetoxy group of AAEMA reacts with the primary amine group to form an imine, or Schiff base. In a preferred embodiment, the primary amine is triethyleneglycoldiamine. This reaction proceeds as follows:

R—NH$_2$ +

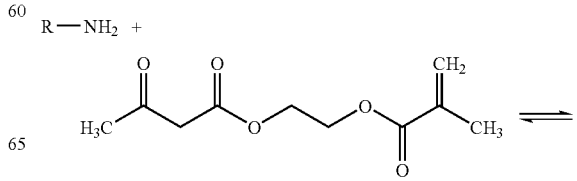

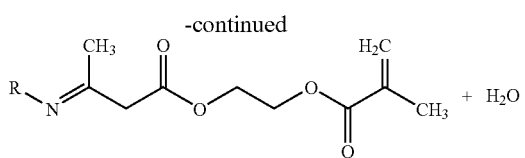

wherein R represents the remainder of the amine. Other amine groups may also react with AAEMA. This reaction is followed by electron re-arrangement favoring the beta carbon of the acetoacetoxy group:

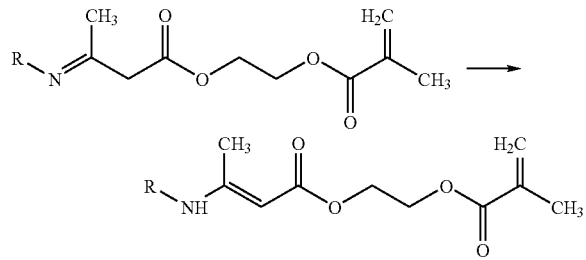

It should also be appreciated that the amine groups can also react with AAEMA ester groups to form an amide:

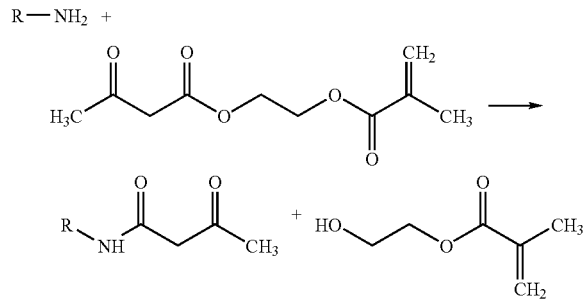

Analytical testing using a Liquid Chromatography Mass Spectrometer (LC-MS) demonstrates that the imine formation reaction takes place more readily than the amide formation reaction. Further analytical testing using a Gas Chromatograph Mass Spectrometer (GC-MS) indicates that less than 10 percent of the AAEMA reacted in the amide formation reaction. Additional testing confirms that increasing the molar ratio of AAEMA to amine increases the number of amine functional groups that react with AAEMA.

While the preferred embodiment of the present invention has been illustrated with the reaction of an AAEMA and a polyether amine (such as polyoxypropylenetriamine), other multi-carbonyl methacrylate chemicals, and other amines may also be used. By using chemicals with slightly different properties, the resulting primer can effectively adhere to a wide variety of surfaces, such as glass, metal, sheetrock, etc., to act as a primer for other applications.

Comparative testing on the adhesion promoting activity of the improved primer of the present invention was performed both in a laboratory (with an instrument that tests adhesion) and in the field by professional nail technicians. Laboratory testing showed that the primer functioned better than its ingredients (amine, AAEMA, and ethanol) individually. More importantly, the nail primer of this invention worked better than all other commercially available nail primers tested.

The following procedure was used in the laboratory testing. First, a clean keratin substrate (hoof) was coated with the tested primer. A system utilizing ethyl methacrylate monomer liquid and a methacrylate copolymer powder was applied to the top of the primed hoofs. After the monomer and copolymer completely polymerized, adhesion testing apparatus utilizing a computer controlled assembly, including a sharp blade held at a precise angle to the surface of the hoof, was used to peel or delaminate the methacrylate polymer from the coated keratin substrate at a predetermined speed. The force needed to delaminate the polymer was detected and recorded by the computerized control system. The greater the force needed to peel or delaminate the polymer from the keratin substrate, the stronger the adhesive bond was to the keratin substrate. Table 1 illustrates the results of the laboratory tests:

TABLE 1

| | Adhesion Strength N | Standard Deviation N | Main Ingredients | Company |
|---|---|---|---|---|
| Advanced Formula Primer | 300 | 65 | Methacrylic acid, Isobutyl Methacrylate | Pinnacle |
| X-Strength Primer | 340 | 60 | Methacrylic acid, Isobutyl Methacrylate | Star Nail |
| Original Non-Lifting | 400 | 65 | Methacrylic acid, Isobutyl Methacrylate | International. Nail Manufacturers |
| No Lift Primer | 490 | 105 | 100% Methacrylic acid | No Lift Nails |
| Bondex | 500 | 80 | Methacryloyloxyethyl maleate, ethyl acetate | O.P.I |
| Covalently Bonding Primer | 570 | 140 | Polyoxypropylenetriamine, AAEMA, Ethanol | Creative Nail Design |

The improved nail primer of the present invention shows average adhesion strength of 570 N. The strongest commercially available primer had adhesion strength of only 500 N.

The significant increase in strength achieved by the disclosed primer can be largely attributed to its ability to covalently bond to the nail plate. As was previously discussed, presently available primers, including those identified in Table 1 (other than the present invention), are bonded to the nail plate via hydrogen bonding. In contrast, applicant's primer takes advantage of the greatly increased bond strengths attained through covalent bonding.

Obviously, with individual differences in both keratins and nail surfaces, a number of covalent reaction mechanisms are possible. It is anticipated, however, that two reactions will dominate. Because of the surprisingly high level of adhesion, we believe our data shows that the dominant reaction involves a direct, continuous series of covalent bonds between the keratin and the enhancement polymer. In the first, ester groups in the primer react with amines in keratin:

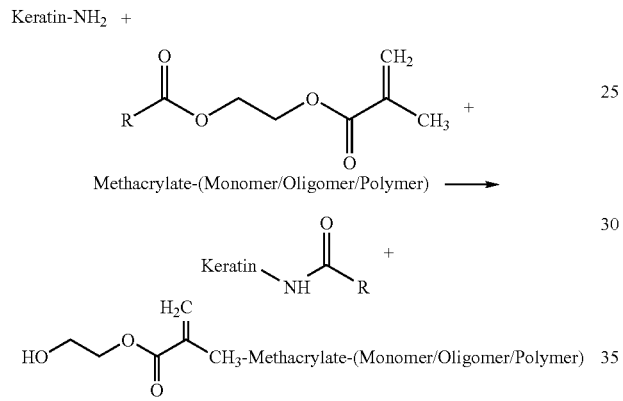

where R is the rest of the primer. In the alternative reaction, amines in the primer react with carboxylic groups in keratin:

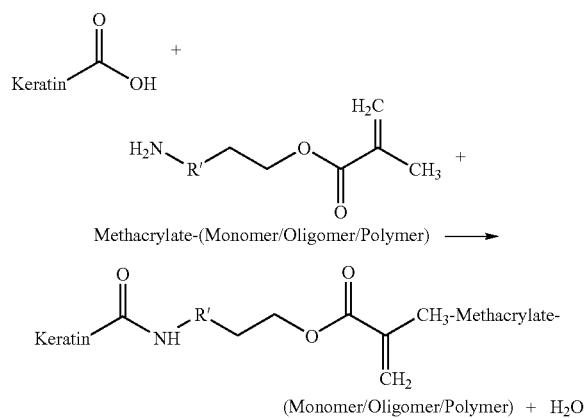

where R' is the rest of the primer.

In any given case, one reaction might dominate over the other, or both reactions may proceed simultaneously. Those of skill in the art will appreciate that it is not the precise reaction mechanism that is important, but rather the fact that covalent bonding, via one or more mechanisms, is occurring. This is the advance that arguably will make all previous nail primers obsolete.

Confirmatory data was also collected in field tests. In a two month study, 18 nail technicians performed tests on a total of 429 clients. The tests showed that the client's nail enhancements were less likely to lift when using the primer of the present invention. Moreover, while discoloration of nail enhancements is inevitable when using a primer that contains methacrylic acid, use of the primer of the present invention eliminated such discoloration. To date, the improved primer of the present invention has been field tested on 4,582 people yielding equally successful results.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

We claim:

1. An adhesion promoter composition comprising:
   (a) a solvent which is free of carbonyl groups; and
   (b) at least one imine of acetoacetoxy ethylmethacrylate, wherein the imine is formed by reacting acetoacetoxy ethyl methacrylate with a polyetheramine, wherein the polyetheramine is selected from the group consisting of triethyleneglycoldiamine, polyethyleneglycolamine, polyethyleneglycoltriamine, polyoxypropyleneamine, polyethyleneglycol-polyoxypropyleneamine, polyoxypropylenediamine, polyoxypropylenetriamine, polyethyleneglycol-polyoxypropylenediamine and polyethyleneglycol-polyoxypropylenetriamine.

2. The composition according to claim 1 wherein the polyetheramine is triethyleneglycoldiamine.

3. The composition according to claim 1 wherein said solvent is a $C_1$-$C_5$ monohydric alcohol.

4. The composition according to claim 3 wherein the solvent is ethanol.

5. The composition according to claim 1 wherein the polyetheramine is polyethyleneglycolamine.

6. The composition according to claim 1 wherein the polyetheramine is polyethyleneglycoltriamine.

7. The composition according to claim 1 wherein the polyetheramine is polyoxypropyleneamine.

8. The composition according to claim 1 wherein the polyetheramine is polyethyleneglycol-polyoxypropyleneamine.

9. The composition according to claim 1 wherein the polyetheramine is polyoxypropylenediamine.

10. The composition according to claim 1 wherein the polyetheramine is polyoxypropylenetriamine.

11. The composition according to claim 1 wherein the polyetheramine is polyethyleneglycol-polyoxypropylenediamine.

12. The composition according to claim 1 wherein the polyetheramine is polyethyleneglycol-polyoxypropylenetriamine.

* * * * *